(12) United States Patent
Wrobel et al.

(10) Patent No.: US 9,267,922 B2
(45) Date of Patent: Feb. 23, 2016

(54) METHOD AND SYSTEM FOR PRODUCT SUPPLY CHAIN ASSURANCE

(76) Inventors: Miroslaw Wrobel, Charlottetown (CA); Jason S. T. Kotler, Toronto (CA)

(*) Notice: Subject to any disclaimer, the term of this patent is extended or adjusted under 35 U.S.C. 154(b) by 357 days.

(21) Appl. No.: 13/825,293

(22) PCT Filed: Sep. 21, 2011

(86) PCT No.: PCT/CA2011/050581
§ 371 (c)(1),
(2), (4) Date: Jul. 11, 2013

(87) PCT Pub. No.: WO2012/037683
PCT Pub. Date: Mar. 29, 2012

(65) Prior Publication Data
US 2015/0033863 A1     Feb. 5, 2015

Related U.S. Application Data (60) Provisional application No. 61/385,028, filed on Sep. 21, 2010.

(51) Int. Cl.
| | | |
|---|---|---|
| G01N 29/02 | (2006.01) | |
| G01N 29/36 | (2006.01) | |
| G01N 29/04 | (2006.01) | |
| G01N 29/024 | (2006.01) | |
| G01N 29/34 | (2006.01) | |
| G01N 29/44 | (2006.01) | |

(52) U.S. Cl.
CPC .............. *G01N 29/02* (2013.01); *G01N 29/024* (2013.01); *G01N 29/043* (2013.01); *G01N 29/348* (2013.01); *G01N 29/36* (2013.01); *G01N 29/4445* (2013.01); *G01N 29/4454* (2013.01); *G01N 2291/021* (2013.01); *G01N 2291/022* (2013.01); *G01N 2291/0258* (2013.01); *G01N 2291/048* (2013.01); *G01N 2291/102* (2013.01)

(58) Field of Classification Search
CPC ... G01N 29/02; G01N 29/024; G01N 29/043; G01N 29/36; G01N 29/348; G01N 29/4445; G01N 29/07
USPC .................... 73/632, 579, 596–600, 602, 620
See application file for complete search history.

(56) References Cited

U.S. PATENT DOCUMENTS

| | | | | |
|---|---|---|---|---|
| 3,780,570 A | * | 12/1973 | Collins | 73/600 |
| 3,886,793 A | * | 6/1975 | Cramer et al. | 73/167 |
| 3,960,007 A | * | 6/1976 | Swensen | 73/629 |
| 4,208,915 A | * | 6/1980 | Edwards | 73/620 |
| 4,332,016 A | * | 5/1982 | Berntsen | 367/7 |
| 4,884,696 A | * | 12/1989 | Peleg | 209/545 |
| 5,062,299 A | * | 11/1991 | Davis et al. | 73/609 |

(Continued)

FOREIGN PATENT DOCUMENTS

| | | |
|---|---|---|
| CA | 2510972 | 12/2006 |
| JP | 2005098744 | 4/2005 |
| KR | 20090041473 | 4/2009 |

*Primary Examiner* — Helen Kwok (57) ABSTRACT

A method and system for determining the purity and authenticity of a substance being transported in a container. A coded signal is first passed through the container and its contents thereby generating an identifier. When the container reaches its destination, a second signal is passed through the container and its contents thereby generating a second identifier. The first and second signals are compared to determine if the substance inside the container has been altered.

20 Claims, 6 Drawing Sheets

(56) References Cited

U.S. PATENT DOCUMENTS

| | | | |
|---|---|---|---|
| 7,878,062 B2 * | 2/2011 | Wrobel | 73/579 |
| 8,756,998 B1 * | 6/2014 | Joplin | 73/596 |
| 2003/0167848 A1 * | 9/2003 | Glaser et al. | 73/597 |
| 2005/0155430 A1 * | 7/2005 | Hutchins et al. | 73/602 |
| 2007/0100578 A1 * | 5/2007 | Wrobel | 702/159 |
| 2011/0128120 A1 | 6/2011 | Libby | |
| 2012/0111118 A1 * | 5/2012 | Keeton et al. | 73/620 |

* cited by examiner

METHOD AND SYSTEM FOR PRODUCT SUPPLY CHAIN ASSURANCE

FIELD OF THE INVENTION

The present invention relates generally to the field of quality assurance systems, and more particularly, to a method and system for product and sub-product supply chain assurance, for example for food products or other consumer and/or industrial goods.

BACKGROUND OF THE INVENTION

Various methods and systems are known for securely transmitting data products (that is, information or similar virtual or non-physical mediums), encrypting same for transport, or otherwise determining whether the data first sent matches the data as received. In this manner, any tampering of data long a communications or transport network can be identified. The secure transmission of data has become essential to modern enterprises, including for use in business, government and military applications.

Recently, greater attention has been paid to the secure transport of non virtual matter food and substance materials. In a Dec. 3, 2004 Washington Post article, the former Health and Human Services Secretary of the United States, Tommy G. Thompson warned that a terrorist attack on the food supply is an easy target. Based on information from the American Association for the Advancement of Science, the U.S. Food and Drug Administration presently inspects less than 2% of the food coming into the United States, while 13% of food is imported. Various Homeland Security Newswire reports have identified the concern for safety in the food supply chain, including those entitled, "Food Safety Products: Global Demand to Reach $2.9 Billion in 2014" published Apr. 21, 2010; "Obama Heralds Food Safety Act" published Jul. 8, 2010; and "Regulators Cannot Cope With Food Counterfeiting, Contamination" published Feb. 17, 2009. Accordingly, there is a need in the art for improved methods and systems for ensuring the safe delivery, transport and storage of materials in the food supply.

Prior art solutions for determining whether a substancesubstance in a container has been tampered with as it is transported through the supply chain have generally been invasive, where the container must be opened to make a determination as to the authenticity of the substance within the container. This is problematic as it takes up a great deal of time, and also cannot be applied to substances that are corrupted when exposed to air, or which must be delivered to an end user in a sealed container. Other prior art solutions rely on on-site laboratory solutions such as infrared spectrometry that are expensive and require a significant amount of overhead. Furthermore, the container must be opened, or the testing mechanisms are not easily transportable, or able to be applied at different points in the supply chain.

Some examples of such problems associated with counterfeit substances exist in the industrial chemical, alcohol, consumer products industries, and consumer cosmetics industries such as perfumes. Counterfeit products are unregulated and often pose public health risks, as is the case with counterfeit baby formula and wine and spirits, as well as damaging the goodwill associated with a company's brand and negatively affecting the producer (brand) company's profits. There is a further need in the art for improved methods and systems for ensuring the safe delivery, transport and storage of various materials susceptible to contamination en route during deliver or other transport, or during storage, whether for long or short periods of time. Other factors that could affect a substance in transport include product degradation from exposure to mishandling, environmental forces, improper packaging or sealing, known and classified mishandling of degradation events, and generally being no longer fit for use, such as by virtue of product expiration dates or shelf-lives. There is a further need in the art for a method and system for ensuring the integrity of substances especially substances through a supply chain in a non-invasive manner.

SUMMARY OF THE INVENTION

The present invention provides a method and system for product supply chain assurance, whereby a product provided with an identifier prior to transport, and subsequently provided with an identifier after transport. If the identifier has altered, a warning is issued that the product has been tampered with, or has otherwise become contaminated.

According to one embodiment of the invention, there is provided a method for determining the purity or authenticity of a substance being transported in a container through a supply chain comprising providing an entry transmitter for generating a first multi-frequency coded ultrasonic signal and an entry receiver for receiving the first signal after it has passed through the container and the substance, generating an entry identifier of the substance in the container based on the first signal, recording the entry identifier at an entry point of the supply chain, transporting the substance in the container to a destination, providing an exit transmitter for generating a second multi-frequency coded ultrasonic signal and an exit receiver for receiving the second signal after it has passed through the substance and the container, generating an exit identifier of the substance in the container based on the second signal, and comparing the entry identifier and the exit identifier to determine whether the substance in the container has been altered during travel through the supply chain. In some embodiments, the container is permeated with the signals, then the substance is identified. Also, the container's characteristics may or may not form part of the entry and/or exit identifiers.

According to one aspect of this embodiment, the method further comprises the step of storing on an entry identifier database, the entry identifier.

According to another aspect of this embodiment, the method further comprises the step of determining whether a particular substance in a container has a corresponding entry identifier stored in the identifier database and if it does, the recording is recorded based on the corresponding entry identifier stored in the database.

According to another aspect of this embodiment, if the entry identifier and the exit identifier do not match, further comprising the step of storing the exit identifier in a counterfeit database, whereby the counterfeit database maintains a listing of identifiers associated with counterfeit or tampered with substances.

According to another aspect of this embodiment, the substance is selected from the group comprising liquid fuels, consumer beverages, milk, pet beverages, alcohols, industrial chemicals, paints and cosmetic substances. The substance may be a liquid, solid or multiphase sub stance.

According to another aspect of this embodiment, the entry transmitter and the entry receiver comprise a device having a first portion adapted to be positioned on one the of the container and housing the entry transmitter and a second portion adapted to be positioned on another side of the container and housing the entry receiver.

According to another aspect of this embodiment, the exit transmitter and the exit receiver comprise a handheld device having a first portion adapted to be positioned on one the of the container and housing the exit transmitter and a second portion adapted to be positioned on another side of the container and housing the exit receiver.

According to another aspect of this embodiment, the substance and the container are unaltered by the method.

According to another aspect of this embodiment the step of comparing includes a permissible deviation allowance between the entry identifier and the exit identifier prior to determining that the substance in the container has been altered.

According to another embodiment of the invention, the entry transmitter and the entry receiver are coincidental with each other, whereby the signal reflects off a surface of said container.

According to another embodiment of the invention, the first and second ultrasonic signals are supplemented with another signal source.

According to another embodiment of the invention, the exit identifier is generated by passing the second ultrasonic signal through the same portion of the container where the first ultrasonic signal passed through to generate said entry identifier.

According to another embodiment of the invention, there is provided system for determining the purity or authenticity of a substance being transported in a container through a supply chain including an entry transmitter for generating a first multi-frequency coded ultrasonic signal and an entry receiver for receiving the first signal after it has passed through the substance and the container, a means for generating an entry identifier of the substance in the container based on the first signal, a recorder for recording the entry identifier at an entry point of the supply chain, a means for transporting the substance in the container to a destination, an exit transmitter for generating a second multi-frequency coded ultrasonic signal and an exit receiver for receiving the second signal after it has passed through the substance and the container, a means for generating an exit identifier of the substance in the container based on the second signal, and a means for comparing the entry identifier and the exit identifier to determine whether the substance in the container has been altered during travel through the supply chain.

According to one aspect of this embodiment, the system includes entry identifier database for storing the entry identifier.

According to another aspect of this embodiment there is provided a means for determining whether a particular substance in a container has a corresponding entry identifier stored in the identifier database.

According to another aspect of this embodiment there is provided a means for storing the exit identifier in a counterfeit database, whereby the counterfeit database maintains a listing of identifiers associated with counterfeit or tampered with substances.

According to another aspect of this embodiment, the entry transmitter and the entry receiver comprise a device having a first portion adapted to be positioned on one the of the container and housing the entry transmitter and a second portion adapted to be positioned on another side of the container and housing the entry receiver. According to another aspect, the entry transmitter and the entry receiver are located in the same position, in which case, the signal could be bounced off a portion of the container back to a measurement point.

According to another aspect of this embodiment, the exit transmitter and the exit receiver comprise a handheld device having a first portion adapted to be positioned on one the of the container and housing the exit transmitter and a second portion adapted to be positioned on another side of the container and housing the exit receiver.

According to another aspect of this embodiment, the substance and the container are unaltered by the system.

According to another embodiment of the invention, there is provided a method for determining the purity or authenticity of a substance being transported in a container comprising providing an exit transmitter for generating a multi-frequency coded ultrasonic signal and an exit receiver for receiving the signal after it has passed through the substance and the container, generating an exit identifier of the substance in the container, comparing the exit identifier with a known entry identifier to determine whether the substance in the container has been altered during travel through the supply chain.

According to an aspect of this embodiment, the method further includes the step of storing a series of known entry identifiers in an identifier database and wherein the comparing step includes comparing the exit identifier with a known entry identifier from the identifier database.

According to another aspect of this embodiment, the exit transmitter and the exit receiver comprise a handheld device having a first portion adapted to be positioned on one the of the container and housing the exit transmitter and a second portion adapted to be positioned on another side of the container and housing the exit receiver. According to another aspect, the exit transmitter and the exit receiver are located in the same position, in which case, the signal could be bounced off a portion of the container back to a measurement point.

According to another embodiment of the invention, there is provided a system for determining the purity or authenticity of a substance being transported in a container comprising an exit transmitter for generating a multi-frequency coded ultrasonic signal and an exit receiver for receiving the signal after it has passed through the substance and the container; a means for generating an exit identifier of the substance in the container, and a means for comparing the exit identifier with a known entry identifier to determine whether the substance in the container has been altered during travel through the supply chain. According to another aspect, the exit identifier may be used to determine how the substance in the container has been altered during travel through the supply chain.

The system according to claim 21, further comprising an identifier database for storing a series of known entry identifiers and wherein the means for comparing compares the exit identifier with a known entry identifier from the identifier database.

According to an aspect of this embodiment the exit transmitter and the exit receiver comprise a handheld device having a first portion adapted to be positioned on one the of the container and housing the exit transmitter and a second portion adapted to be positioned on another side of the container and housing the exit receiver.

BRIEF DESCRIPTION OF THE DRAWINGS

The invention will now be described in more detailed, by way of example only, with reference to the accompanying drawings, in which like numbers refer to like elements, wherein.

DETAILED DESCRIPTION OF THE PREFERRED EMBODIMENTS

The invention relates generally to the transportation of a substance in a container, and in particular, the transportation of a substance in a container through a supply chain. As will be appreciated from the description that follows, the invention provides a method and system that permit for the inspection of a substance at an entry point, an exit point and any point therebetween of a supply chain to determine whether the substance and/or the container have been tampered with during transportation. For the purposes of this description, reference to exit points or exit identifiers refers to any point at which a measurement is taken and should not be construed as an exit point of the supply chain. Rather, an exit point is a point at which a determination is made on whether there has been a change to the substance in the container when compared to a previous point. As will also be described, the invention can also be applied, in some embodiments, to determining whether a substance in a container has been replaced or is otherwise a counterfeit good, for example stored in a container representing a particular brand or quality of substance, but having been substituted for a similar or dissimilar substance prior to transportation. The invention further provides the advantage that a determination may be made with respect to whether the substance in the container has altered or has been altered without the need to open the container. This may be particularly beneficial in supply chains where employees or other individuals coming into contact with the supply chain should not be away of what is in the containers. Employing the invention as described below, allows for supply chain workers to determine whether a product moving through the supply chain has been altered, but without any knowledge of what the product is.

Figure 1:
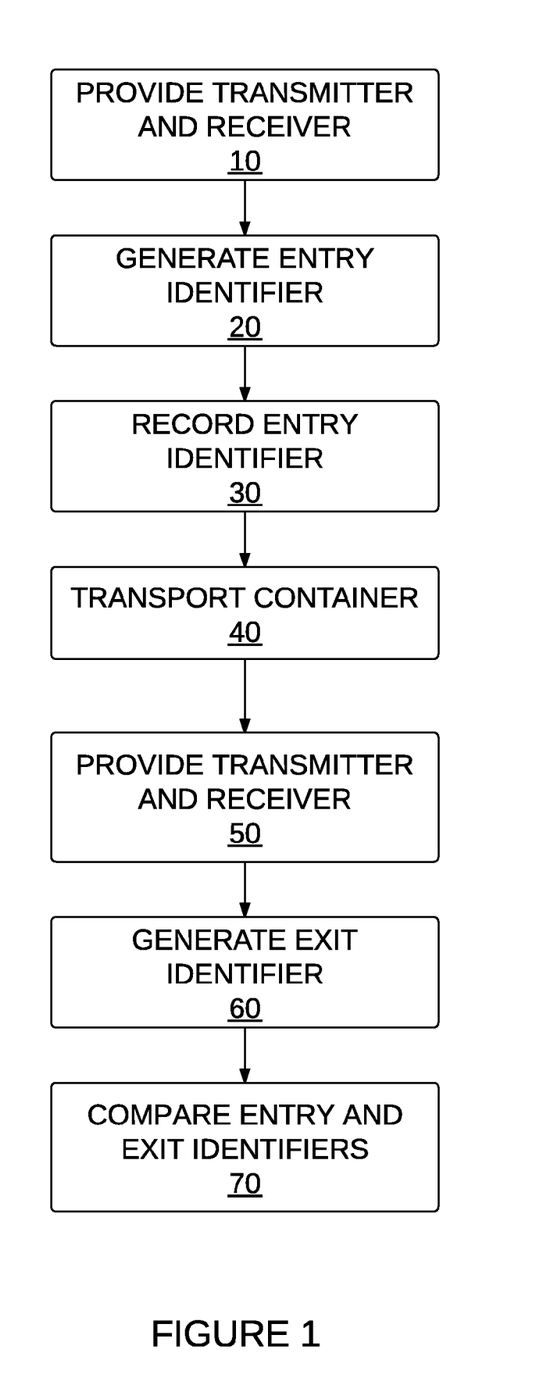
FIG. 1 is a flowchart showing a method according to one embodiment of the invention.

With reference now to FIG. 1, there is shown one embodiment of the invention, where there is provided a method for determining the purity or authenticity of a substance being transported in a container through a supply chain including the step 10 of providing an entry transmitter for generating a first multi-frequency coded ultrasonic signal and an entry receiver for receiving the first signal after it has passed through the substance and the container. One such combination of an entry transmitter and an entry receiver that may be with the invention is described in PCT publication WO 2007/000047, entitled "Advanced Ultrasonic Interferometer and Method Of Non-Linear Classification and Identification of Matter Using Same," the entirety of which is herein incorporated by reference. It is also contemplated that supplemental sources of signals may be used to fine tune or augment the ultrasonic measurements, for example, x-ray, gamma radiation, NMR, capacitance, electromagnets, etc.

In step 20, an entry identifier of the substance in the container is generated based on an interpretation of the first signal after it has passed through the container and the substance. The entry identifier may also be referred to as a fingerprint for the substance in the container that will be unique to specific substances in specific containers. In this manner, even slight deviations or alterations in the substance during transport may be detected. The manner in which the entry identifier is generated is described hereinbelow, and is also discussed in the aforementioned PCT publication.

In step 30, the entry identifier is recorded at an entry point of said supply chain. Alternatively, the entry identifier may be recorded from a sample of the substance in the container, or at any point in the supply chain from where a baseline identifier may be taken. Following recordal of the entry identifier, the substance in the container is transported to a destination in step 40.

At a destination, or other exit point, or alternatively at an intermediary point in the supply chain, an exit transmitter for generating a second multi-frequency coded ultrasonic signal and an exit receiver for receiving the second signal after it has gone through the substance and the container are provided in step 50. The exit transmitter and receiver may be functionally equivalent to the entry transmitter and entry receiver. In one embodiment, the transmitter and receiver combination are provided in a handheld device that may be one and the same device transported from the entry point to the exit point.

In step 60, an exit identifier is generated of the substance in the container as it exits a transport segment within the supply chain, based on the second signal The exit identifier is generated in an analogous manner as the entry identifier discussed above. Next, in step 70, the entry identifier and the exit identifier are compared to determine whether the substance in the container has been altered during travel through the supply chain. The comparison may be carried out by a computer that produces an alert, for example, when the entry identifier and the exit identifier do not match, or alternatively, when they differ to a degree beyond a predetermined allowable deviation. Alternatively, the comparison may be carried out manually by a user or technician who observes the two readings and removes those containers carrying a substance that has evidence of tampering, contamination, or product degradation. In some embodiments, a permissible deviation allowance between the entry identifier and the exit identifier is provided for prior to determining that the substance in the container has been altered.

The entry and exit identifiers are preferably provided in the form of an analog or digital signal that may be compared with each other using known signal comparison techniques. In carrying out the comparison, a typical unit of measurement is not created, so that the comparison can be done without knowledge of the substance within the container. The resulting numerical values (analog—as in a tape recorder comparison example or digital signal conversion) is analyzed as a vector output value, based on the raw signals. The output vector value result can even be recorded manually, then compared to a matching result upon exit. Since only the resulting vector values are important to the system, only these analog/digital results would need to be recorded, and therefore, product secrecy can be maintained if desired. Of course, other known measurement data resulting in a product classification may be useful in some instances, and this data may also be included.

Figure 2:
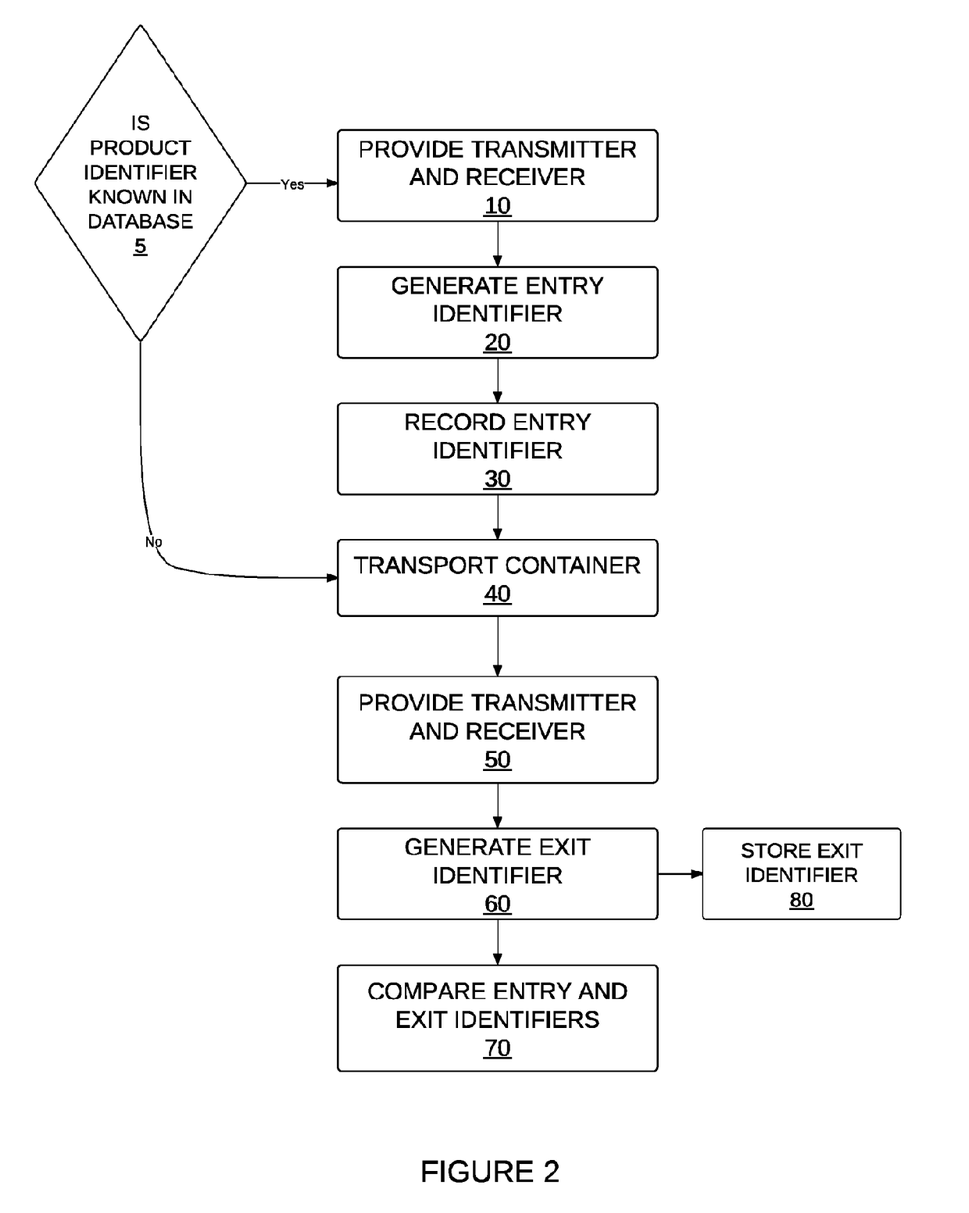
FIG. 2 is a flowchart showing another embodiment of the method according to the invention.

According to another embodiment of the invention, an entry identifier database may be provided that stores information on known containers and substances that are permissible and indicative of being authentic. In this embodiment, if a substance in a container is known to have a particular entry identifier, the step of determining an entry identifier may be skipped altogether. In this embodiment, only exit identifiers are determined and compared to the identifier stored in the identifier database. Such an entry identifier database may be populated by operators of the supply chain, manufacturers of the substances, or other parties having an interest in ensuring that the substance in the container is unaltered during travel either through the supply chain or through portions thereof. FIG. 2 illustrates this embodiment of the invention, where a determination is first made in step 5 as to whether the substance in the container has a known identifier that should be met at an exit point from the supply chain, and further, if this is the case, then an entry identifier is recorded directly from information held in the database. The unique identifiers could be determined at source at step 20, non-invasively using suggested methods in this description, or alternatively via empirical lab tests or other measurement methods. The identifier in step 20 can then be confirmed or reaffirmed prior to transport.

The method may further include the optional step 80 of storing the exit identifiers in a counterfeit database, and particularly where the exit identifier does not match the entry identifier. In this manner, a database may be maintained that includes identifiers characteristic of substances that have been tampered with, are counterfeit, or have evidence of product degradation or contamination, or otherwise known to have a deviation from an originating source of the substance. In this manner, an identifier may be obtained at any point in the supply chain, or indeed at the end user level, and if the identifier corresponds with one stored in the database and known to be indicative of a counterfeit, or similar substance, it can be removed from the supply chain immediately.

In a preferred embodiment, the second signal is passed through the container at a location coinciding with that where the first signal was passed through the container to generate the first identifier. In this manner, the first identifier and the second identifier are generated in the most reasonably consistent manner.

It is contemplated that the invention may be applied to the transport or movement of a substance through a supply chain, where the substance may be liquid or gaseous fuels, biological agents, drugs, consumer food and beverages, milk, pet food, alcohols, industrial chemicals, paints and cosmetics substance. The substance may be a liquid, solid, or a multiphase composition including one or more liquids and/or solids.

Figure 3:
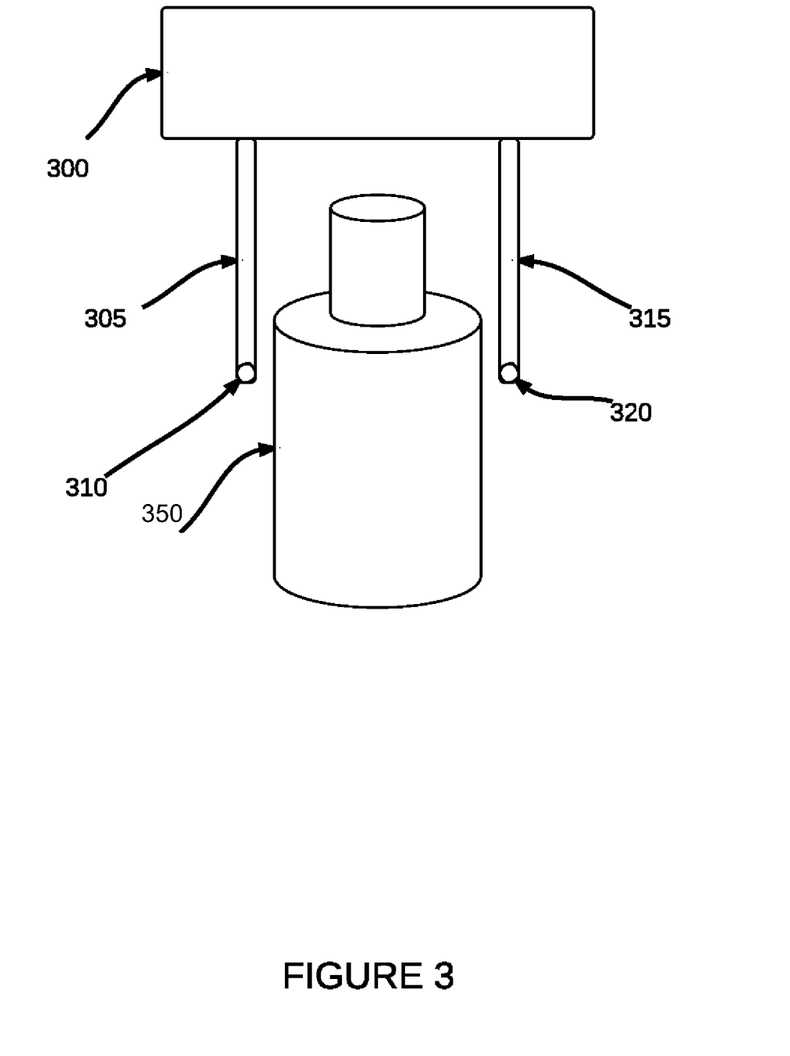
FIG. 3 shows one embodiment of a device for obtaining an identifier according to the invention.

Referring now to FIG. 3, there is shown one embodiment of a device 300 incorporating both the entry transmitter 310 and the entry receiver 320. The device 300 includes first portion 305 adapted to be positioned on one side of the container 350 and housing the entry transmitter 310 and a second portion 315 adapted to be positioned on another side of the container 350 and housing the entry receiver 320. Preferably, a similar device may be used at an exit to the supply chain and includes the exit transmitter and the exit receiver. In operation, the substance and the container are unaltered by the device 300, or by the transmission of the signal through the substance for generating the respective identifiers. It is also contemplated that the product label or other unique label identifier (such as a UPC, QR Code, RFID, etc.) can be read to denote the product type inside, container type, and where on the container itself the device needs to aim to measure the product. Furthermore, a visible or untraceable "target" on container that is integrated with measuring device may be provided, as would be important to containers that have a unique packaging, such as perfumes.

Figure 4:
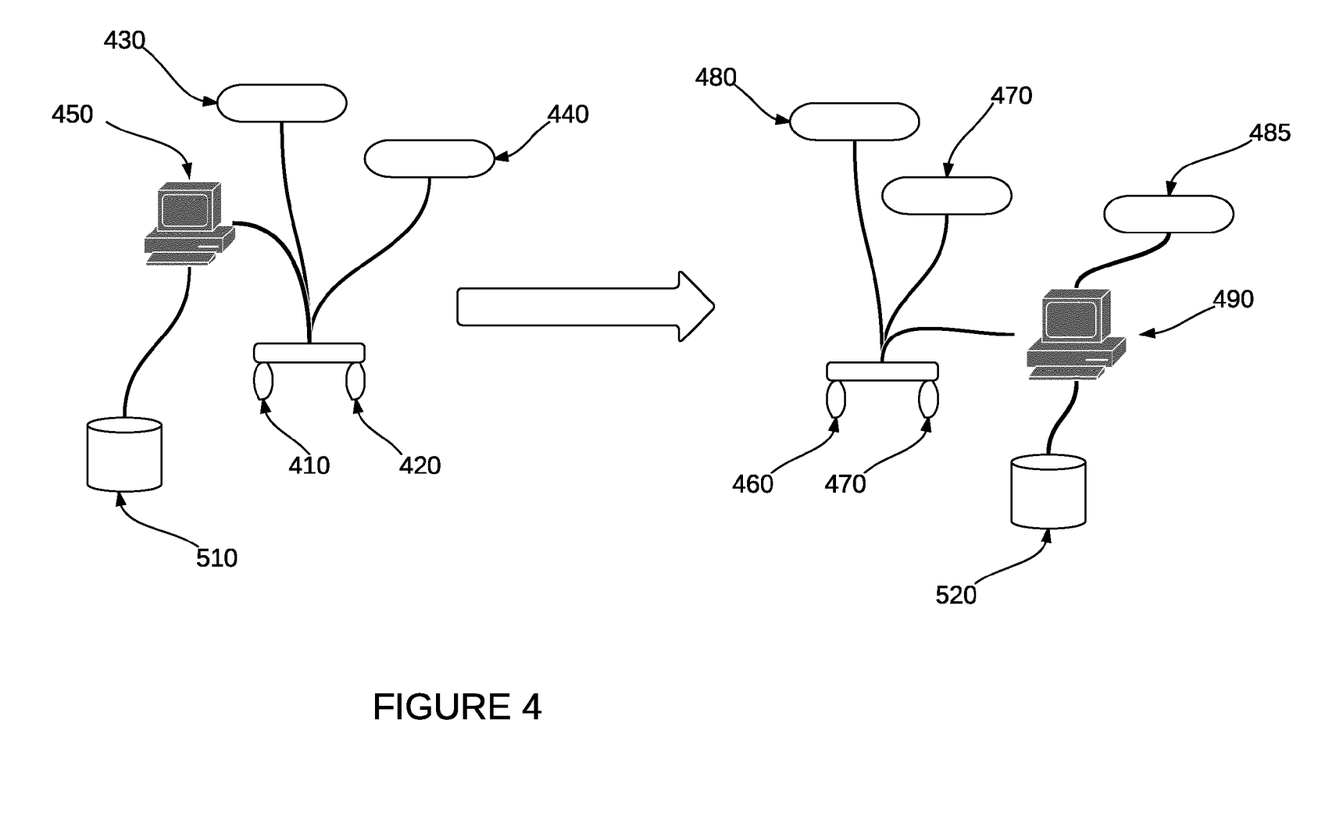
FIG. 4 shows one embodiment of a system for carrying out the method according to the invention.

Referring now to FIG. 4, there is shown a system 400 for carrying out the method of the invention as herein described. The system 400 preferably includes an entry transmitter 410 for generating a multi-frequency coded ultrasonic signal and an entry receiver 420 for receiving the signal after it has passed through the substance and the container. A means for generating an entry identifier 430 provides for a unique identifier for each particular substance and container combination as described herein. The means for generating 430 is preferably a processor embedded within the entry receiver 420, but may also be a computer system 450 in communication with the entry transmitter 410 and with the entry receiver 420. A recorder 440 is provided for recording the entry identifier at an entry point of the supply chain. The recorder may also be provided by the computer system 450.

A means for transporting the substance in the container to a destination is also provided. The invention is not limited to any particular means for transporting, but these may include, via pipeline, freight train, truck, ship, airplane, etc.

The system 400 preferably also includes an exit transmitter 460 for generating a multi-frequency coded ultrasonic signal and an exit receiver 470 for receiving the signal after it has passed through the substance and the container. A means for generating an exit identifier 480 is also provided. The means for generating 480 is preferably a processor embedded within the exit receiver 470, but may also be a computer system 490 in communication with any of the aforementioned components. It is also contemplated that the entry and exit receivers and transmitters are provided by a single device. A means for comparing 485 the entry identifier and the exit identifier is provided to determine whether the substance in the container has been altered during travel through the supply chain. The means for comparing may be any computer system 495 either in communication with the exit receiver 470, and otherwise has available to it the entry identifier.

While the system 400 refers generally to means for carrying out certain steps, it will be appreciated by those skilled in the art that such means may be provided in the form of a software module provided on a computer system in communication with other elements of the system. Such a computer system is shown generally in FIG. 5 where there is shown an exemplary computer system 10 on which various elements of the invention may be implemented and otherwise organized for carrying out the invention. The computer system 10 has a number of physical and logical components, including a bus 12 and a CPU 14 attached to the bus 12 for performing the processing functions of the computer system 10. Also provided are read only memory (ROM) 16 and random access memory (RAM) 18 for use by the CPU 14. An input/output interface 20 allows for input to be received from one or more devices, such as a keyboard, a mouse, etc., and outputs information to output devices, such as a display and/or speakers. A network interface 22 enables communication with other systems. Non-volatile storage means 24 stores the operating system and programs. The non-volatile storage means 24 may include a hard disk drive, a network drive, or other devices as are known in the art. During operation of the computer system 10, the operating system, the programs and data may be retrieved from the non-volatile storage means 24 and placed in RAM 18 to facilitate execution. An analog/digital signal converter (not shown) may be provided to convert the measured signals into a form suitable for computer processing. Alternatively, only analog signals may be recorded and compared directly to each other. The identifiers as herein described will be unique, whether in analog or digital form.

Figure 5:
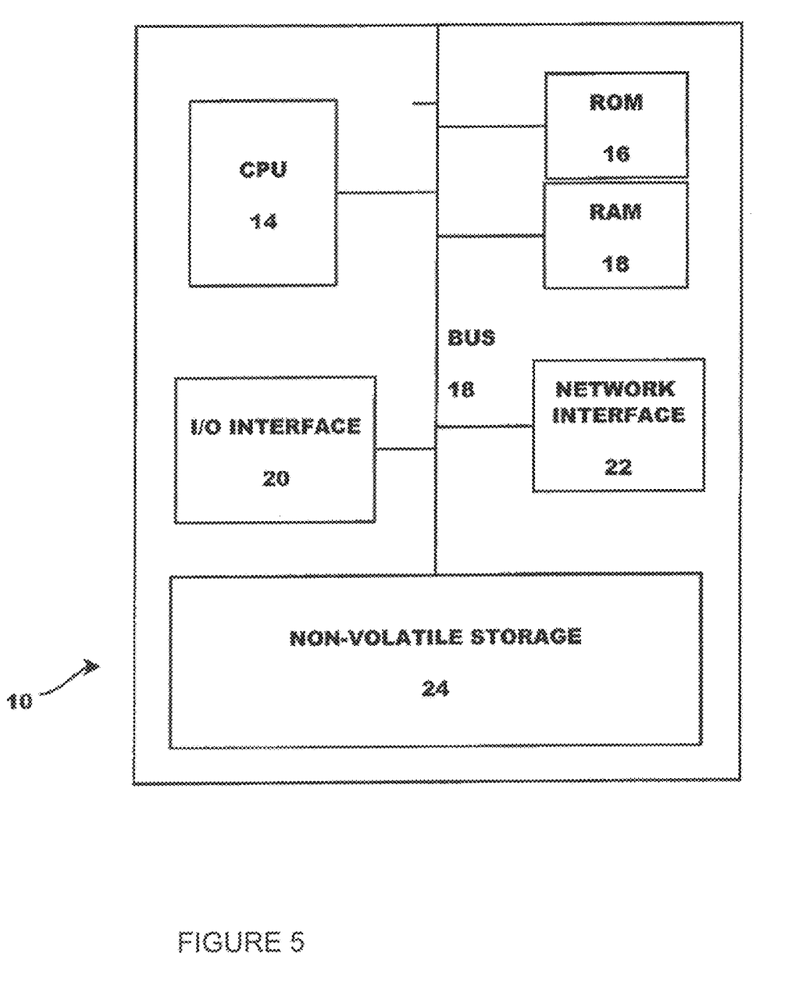
FIG. 5 shows a computer system on which various processes of the invention may be carried out.

In one aspect of the invention, the system further includes and entry identifier database 510 for storing the entry identifier. In this embodiment, a database 510 of known entry identifiers can be populated and stored on a server so that substances and/or containers known to be authentic can have their identifiers stored in a central database. In this aspect, the system further includes a means for determining whether a particular substance in a container has a corresponding entry identifier stored in the identifier database 510. The means for determining may be provided, for example, by a software module on the computer system 480. If there is a corresponding entry in the identifier database 510, then the substance in the container may proceed directly through the supply chain without having an identifier generated at an entry point to the supply chain.

The invention also contemplates the provision of a means for storing the exit identifiers in a counterfeit database 520. The means for storing may be a software module on the computer system in communication with the counterfeit database 520. The counterfeit database 520 preferably maintains a listing of identifiers associated with counterfeit or tampered with substances. In this manner, where a substance in a container is delivered to a destination, but has along the route or from the origin point been provided as a counterfeit substance, a determination may be made upon generation of the identifier that such an identifier is one known to be a counterfeit one.

Figure 6:
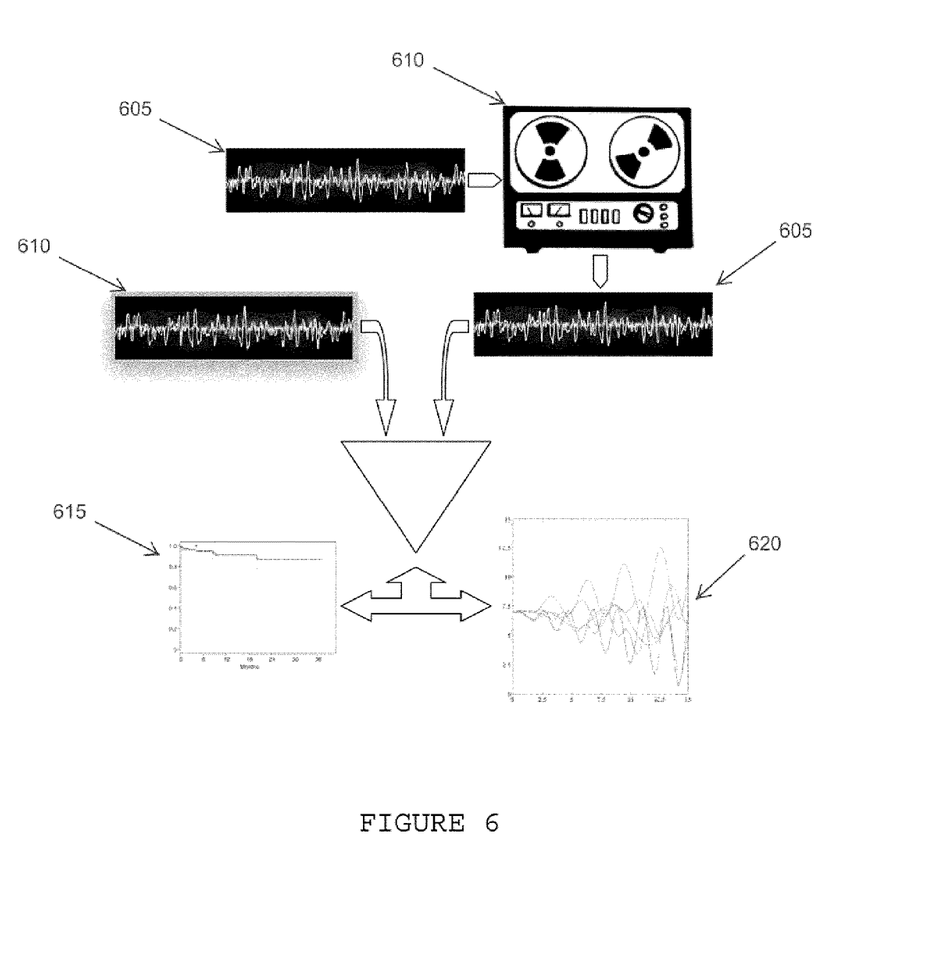
FIG. 6 shows a system diagram of the measurements taken according to the invention.

Referring to FIG. 6, there is shown an embodiment of the invention where an entry identifier 605 is generated in the form of an analogue signal, and stored in a database 610. An exit identifier 610 is then generated and compared with the stored entry identifier 605 using known comparator techniques. Where the identifiers are a match, a zero comparator reading results, as shown at 615. Alternatively, if the signals do not match, a non-zero comparator reading results as shown at 620.

As described above, the invention may use a multi-frequency coded ultrasonic signal to generate the entry and exit identifiers in such a manner that the substance and the container are unaltered during generation of the entry and exit identifiers, and thereby characterize the substance in the container in a non-intrusive manner. One such system to generate the entry and exit identifiers uses piezoceramic transmitters and receivers to transmit the coded multi-frequency signal and receive same after it has passed through the substance in the container. The phase of each of the frequencies in the coded multi-frequency signal is determined using conventional techniques, and these phases in various combinations provide measurements of the travel times of the particular frequencies. Based on this information, the density, the bulk modulus, the speed of sound and the time of flight of the continuous signal in the substance can be characterized.

The natural, usually non-desirable, higher harmonic property of ultrasonic piezoceramic transducers is also exploited by this invention. Typically, it is impossible to penetrate certain materials or objects with higher frequency ultrasonic signals because the attenuation of these signals is too high. However higher harmonics are used in this invention to achieve this penetration. By deploying a lower frequency signal, the higher harmonics are also deployed.

The beating of two frequencies is used to establish a baseline. Any two periodic signals possess a natural common beat period. During one beat period there is no duplication of a phase pair of the two periodic signals. Therefore any valid phase pair can be used to accurately pinpoint a time moment in the beat period. This is used to accurately determine the time of flight of the signal through the substance.

The measurement of the phase parameters and travel times are used to create a profile of the substance in the container. This measured profile is used in a trainable classification system (a non-linear classification system, if necessary) to produce a reliable identifier of the substance in the container. Each piezoceramic transducer has a tendency to generate the higher harmonics of the produced signal. Generally, this natural property of the transducer has been undesirable and has, typically, been reduced by using filters. This property of the transducers is based on the fact that signal generated by transducer is not of an ideal sinusoidal form. The generated signal is a sinusoid, but also it includes some of the higher harmonics. By using this deficiency of the piezoceramic transducer, the higher frequency signals are also generated. Sending the higher frequencies as a small distortion of the ideal sinusoid enhances these higher harmonics. After receiving the reflection the transmitted signals, the primary frequency as well as the harmonics are known, and the phases can be computed even if there is substantial noise accumulated while travelling through the substance.

The use of a quasi-constant pulse or a continuous illumination decreases the intensity of the pressure waves in the substance. An array of phase shifts are collected for all of the frequencies transmitted through the substance. This array of phase shifts is used to compute an array of frequency dependent travel times through the substance. The array of time of flight together with the reference density, is sufficient to uniquely classify the substance or the state of a process. The accurate time of flight for each frequency is computed using the base line travel time measurement together with the phase measurements across the spectrum (i.e. all of the colours of sound) to form the unique identifier of the substance in the container.

Various modifications and variations of the invention are contemplated without departing from the spirit and scope of the invention which is defined by the claims that follow. For example, it is contemplated that sensors forming the transmitters and receivers and described herein may be permanently attached to a container, such that only components for generating the identifier, recording and further processing same are provided at points where measurements are taken. That is, containers may have built-in sensors that form part of the security and thus making it more difficult to provide counterfeit containers. Furthermore, markers on the container may be provided that include computer readable instructions on where the signal should be passed through the container to obtain the most accurate reading. For example, a portion of the container may be modified to produce a unique marker, apart from that provided by the rest of the container or from the container in combination with the substance within it, making it difficult for a counterfeit container to be passed through the supply chain.

The invention claimed is:

1. A method for determining the purity or authenticity of a substance being transported in a container through a supply chain comprising:
  a. providing an entry transmitter for generating a first multi-frequency coded ultrasonic signal and an entry receiver for receiving said first signal after said first signal has passed through the container and through the substance;
  b. generating an entry identifier of the substance in the container based on said first ultrasonic signal;
  c. recording said entry identifier at an entry point of said supply chain;
  d. transporting the substance in the container to a destination;
  e. providing an exit transmitter for generating a second multi-frequency coded ultrasonic signal and an exit receiver for receiving said second signal after it has passed through the substance and the container;
  f. generating an exit identifier of the substance in the container based on said second ultrasonic signal; and,
  g. comparing said entry identifier and said exit identifier to determine whether the substance in the container has been altered during travel through the supply chain.

2. The method according to claim 1, further comprising the step of storing on an entry identifier database, said entry identifier.

3. The method according to claim 2, further comprising the step of, before step a., determining whether a particular substance in a container has a corresponding entry identifier stored in said identifier database and if said particular substance does, said step c. of recording is recorded based on said corresponding entry identifier stored in said database.

4. The method according to claim 1, wherein if said entry identifier and said exit identifier do not match, further comprising the step of storing said exit identifier in a counterfeit database, whereby said counterfeit database maintains a listing of identifiers associated with counterfeit or tampered with substances.

5. The method according to claim 1, wherein said substance is selected from a group comprising fuels, consumer beverages, milk, pet beverages, alcohols, industrial chemicals, paints and cosmetic substances.

6. The method according to claim 1, wherein said entry transmitter and said entry receiver comprise a device having a first portion adapted to be positioned on one side of the container and housing said entry transmitter and a second portion adapted to be positioned on another side of the container and housing said entry receiver.

7. The method according to claim 1, wherein said entry transmitter and said entry receiver are coincidental with each other, whereby said first signal reflects off a surface of said container.

8. The method according to claim 1, wherein said first and second ultrasonic signals are supplemented with another signal source.

9. The method according to claim 1, wherein said exit identifier is generated by passing said second ultrasonic signal through the same portion of the container where said first ultrasonic signal passed through to generate said entry identifier.

10. The method according to claim 1, wherein said exit transmitter and said exit receiver comprise a handheld device having a first portion adapted to be positioned on one side of the container and housing said exit transmitter and a second portion adapted to be positioned on another side of the container and housing said exit receiver.

11. The method according to claim 1, wherein the substance and the container are unaltered by the method.

12. The method according to claim 1, wherein said step of comparing includes a permissible deviation allowance between said entry identifier and said exit identifier prior to determining that the substance in the container has been altered.

13. A system for determining the purity or authenticity of a substance being transported in a container through a supply chain comprising:

an entry transmitter for generating a first multi-frequency coded ultrasonic signal and an entry receiver for receiving said first signal after said first signal has passed through the substance and the container;

a means for generating an entry identifier of the substance in the container based on said first signal;

a recorder for recording said entry identifier at an entry point of said supply chain;

a means for transporting the substance in the container to a destination;

an exit transmitter for generating a second multi-frequency coded ultrasonic signal and an exit receiver for receiving said second signal after said second signal has passed through the substance and the container;

a means for generating an exit identifier of the substance in the container based on said second signal;

a means for comparing said entry identifier and said exit identifier to determine whether the substance in the container has been altered during travel through the supply chain.

14. The system according to claim 13, further comprising entry identifier database for storing said entry identifier.

15. The system method according to claim 14, further comprising a means for determining whether a particular substance in a container has a corresponding entry identifier stored in said identifier database.

16. The system according to claim 13, further comprising a means for storing said exit identifier in a counterfeit database, whereby said counterfeit database maintains a listing of identifiers associated with counterfeit, degraded or tampered with substances.

17. The system according to claim 13, wherein said substance is selected from a group comprising substance fuels, consumer beverages, milk, pet beverages, alcohols, industrial chemicals, paints and cosmetic substances.

18. The system according to claim 13, wherein said entry transmitter and said entry receiver comprise a device having a first portion adapted to be positioned on one side of the container and housing said entry transmitter and a second portion adapted to be positioned on another side of the container and housing said entry receiver.

19. The system according to claim 13, wherein said exit transmitter and said exit receiver comprise a handheld device having a first portion adapted to be positioned on one side of the container and housing said exit transmitter and a second portion adapted to be positioned on another side of the container and housing said exit receiver.

20. The system according to claim 13, wherein the substance and the container are unaltered by the system.

* * * * *